(12) United States Patent
Bischoff et al.

(10) Patent No.: US 9,427,822 B2
(45) Date of Patent: Aug. 30, 2016

(54) LASER TREATMENT DEVICE

(75) Inventors: Mark Bischoff, Jena (DE); Elke Ebert, Jena (DE); Karsten Festag, Jena (DE); Carsten Lang, Eisenberg (DE); Markus Sticker, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 2807 days.

(21) Appl. No.: 10/568,465

(22) PCT Filed: Oct. 21, 2004

(86) PCT No.: PCT/EP2004/011928
§ 371 (c)(1),
(2), (4) Date: Feb. 14, 2006

(87) PCT Pub. No.: WO2005/039462
PCT Pub. Date: May 6, 2005

(65) Prior Publication Data
US 2007/0010803 A1    Jan. 11, 2007

(30) Foreign Application Priority Data

Oct. 23, 2003  (DE) .................................. 103 49 296
Oct. 23, 2003  (DE) .................................. 103 49 297

(51) Int. Cl.
*A61F 9/008*     (2006.01)
*B23K 26/04*     (2014.01)
*A61F 9/009*     (2006.01)

(52) U.S. Cl.
CPC .............. *B23K 26/04* (2013.01); *A61F 9/009* (2013.01); *B23K 26/043* (2013.01); *A61F 9/00825* (2013.01); *A61F 2009/00855* (2013.01); *A61F 2009/00872* (2013.01)

(58) Field of Classification Search
CPC ................. A61F 9/008–9/0084; B23K 26/04; B23K 26/043
USPC .................................................. 606/5, 10–13
See application file for complete search history.

(56) References Cited

U.S. PATENT DOCUMENTS

| 5,157,750 | A | * | 10/1992 | Grace et al. .................... 606/10 |
| 5,336,215 | A |   | 8/1994  | Hsueh et al. |
| 5,549,632 | A | * | 8/1996  | Lai .................................... 606/5 |
| 5,645,550 | A |   | 7/1997  | Hohla |
| 5,984,916 | A |   | 11/1999 | Lai |
| 6,210,401 | B1|   | 4/2001  | Lai |
| 6,254,595 | B1|   | 7/2001  | Juhasz et al. |
| 6,312,422 | B1|   | 11/2001 | Dubnack |
| 6,325,792 | B1| * | 12/2001 | Swinger et al. ................. 606/4 |
| 6,373,571 | B1|   | 4/2002  | Juhasz et al. |
| 2001/0021844 | A1 | | 9/2001 | Kurtz et al. |
| 2001/0025173 | A1 | * | 9/2001 | Ritchie et al. ................. 606/10 |
| 2002/0103482 | A1 | | 8/2002 | Scholler et al. |
| 2004/0020983 | A1 | | 2/2004 | Feige et al. |

FOREIGN PATENT DOCUMENTS

| DE | 198 14 095 C2 | 10/1999 |
| DE | 100 52 201 C2 | 5/2002 |
| EP | 0 608 052 A2 | 7/1994 |
| EP | 1 159 986 A2 | 12/2001 |
| WO | WO 01/87199 A2 | 11/2001 |
| WO | WO 03/002008 A1 | 1/2003 |

\* cited by examiner

*Primary Examiner* — David Shay
(74) *Attorney, Agent, or Firm* — Patterson Thuente Pedersen, P.A.

(57) ABSTRACT

The invention relates to an adapter for coupling a laser treatment device to an object for treatment, whereby the adapter has an input side, which may be fixed relative to the laser treatment device, by a locking mechanism and which may be fixed to the object, for alignment of the object relative to the laser treatment device. A scanned laser beam is introduced on the input side, from the laser treatment device, along a beam path to the object with a reference structure. The reference structure lies on the beam path of the adapter and may be optically detected by means of the laser beam scanned over the region.

23 Claims, 4 Drawing Sheets

LASER TREATMENT DEVICE

FIELD OF THE INVENTION

The invention relates to an adapter for coupling a laser processing device with an object to be processed, said adapter comprising an input side, which can be fixated relative to the laser processing device via a locking mechanism, being attachable to the object for positioning of the object relative to the laser processing device, transmitting a laser beam to the object along a beam path, said laser beam having been supplied to the input side by the laser processing device and scanned over a certain region, and comprising a reference structure, in particular relating to the orientation of the adapter. The invention further relates to a laser processing device for such adapter, said device comprising a beam deflecting unit for scanning a laser beam.

BACKGROUND OF THE INVENTION

In material processing by means of laser radiation, laser beam scanning of the zones to be processed on the object is generally employed. The precision of positioning the laser beam usually determines the precision achieved in said processing. Focussing of the laser beam into a processing volume requires exact three-dimensional positioning. Therefore, for high-precision processing it is usually indispensable to hold the object in an exactly defined position relative to the laser processing device. The above-mentioned adapter is intended for such applications because it fixates the object to be processed or imparts a desired shape to the deformable surface of the object to be processed.

This is required, in particular, for micro-processing of materials which have only a low linear optical absorption in the spectral range of the processing laser radiation. For such materials, usually non-linear interactions between the laser radiation and the material are employed, in most cases in the form of an optical breakthrough generated in the focus of the laser beam. Since the processing action takes place only in the laser beam focus, exact three-dimensional positioning of the focal point is indispensable. Thus, an exact depth position of the focus position is required in addition to a two-dimensional deflection of the laser beam. The above-mentioned adapter facilitates this because it ensures constant optical conditions, which are also known with a certain precision, in the beam path to the object, or because known optical conditions, in particular refractive conditions, are present in the beam path when the adapter contacts the object.

A typical application for such an adapter is the ophthalmic surgery procedure known as LASIK, wherein a laser beam is focussed into the cornea on a focal point which is of the order of magnitude of one micrometer. A plasma then forms in the focus, which plasma causes local separation of the corneal tissue. By suitable serial arrangement of the local separation zones generated in this manner, macroscopic cuts are realized and a certain partial volume of the cornea is isolated. A desired change in refraction is then achieved by removal of said partial volume, so that correction of a visual defect is possible.

Exact positioning of the laser beam is indispensable to carry out the method. For this purpose, a contact lens provided with reference marks is known from U.S. Pat. No. 6,373,571, said lens realizing an adapter of the aforementioned type. This contact lens is adjusted by means of a separate measurement device, which results in a relatively complex structure. The aforementioned adapter serves two functions: not only does it ensure the required optical properties for the laser beam to enter the cornea, but it also fixates the eye, preferably with respect to several degrees of freedom, particularly preferably with respect to all possible degrees of freedom. This prevents movements of the eye relative to the laser processing device.

An example of such adapter is described, for example, in WO 03/002008 A1. The adapter referred to therein as "applanation lens" comprises a suction ring, which is attached to the eye by means of suction. Inserted in the suction ring is a glass plate, which is pressed into the suction ring by means of a bracket. The bracket simultaneously also fixes a flange part to the suction ring, which flange part is permanently attached to the laser processing device. The multi-component adapter of WO 03/002008 A1 presses the surface of the cornea flat, thus achieving simple standard geometries. However, this is very inconvenient for the patient. Moreover, applanation of the corneal surface is undesired in some surgical operations.

A further example of an adapter of the aforementioned type is described in EP 1,159,986 A2. It has reticle markings at the edge of a holder, which make visual alignment possible for the surgeon. However, the precision achieved thereby is not always sufficient.

Therefore, it is an object of the invention to improve an adapter or a laser processing device of the aforementioned type such that high-precision laser processing is easily possible.

SUMMARY OF THE INVENTION

This object is achieved by an adapter for coupling a laser processing device with an object to be processed, said adapter comprising an input side which can be fixated relative to the laser processing device via a locking mechanism, being attachable to the object for orientation of the object relative to the laser processing device, transmitting a laser beam to the object along a beam path, said laser beam having been supplied to the input side by the laser processing device and scanned over a certain region, and comprising a reference structure, which reference structure is located in the beam path of the adapter and is optically detectable by means of the laser radiation scanned across said region. The reference structure for alignment of the adapter is preferably detectable with respect to its position.

The object is further achieved by a laser processing device for the use of such an adapter, said device comprising a beam deflecting unit for scanning a laser beam, a detecting unit for optical detection of the reference structure by means of the laser beam, and a control unit reading out the detecting unit, which control unit controls the beam deflecting unit, determines the actual position of the adapter on the basis of the optically detected reference structure and considers said position when controlling the beam deflecting unit.

The reference structure provided in the beam path of the adapter allows the laser processing device to exactly detect the position of the adapter and thus of the object.

However, the function of the adapter according to the invention is not limited to producing an exact alignment or a very precisely known alignment. The laser processing device which can be sensed by the laser beam also allows the function of the laser processing device to be checked in the simplest manner with respect to laser beam deflection. For this purpose, a laser beam is guided over the reference structure during operation of the laser processing device for control purposes; detection of the reference structure is assigned to the corresponding control value of the laser beam deflection, and any deviation between the control value and the actual laser beam deflection is determined from the known position and the assigned control value of the laser beam deflection. This difference can be considered for correction of the deflection control of the laser beam during subsequent operation. Optionally or additionally, if the need for correction exceeds a threshold value, operation of the laser processing device may be blocked.

The laser radiation used in doing so may be identical with the processing laser radiation; however, this need not be the case. Advantageously, the laser processing device will employ the same beam deflection means, e.g. a scanning unit, for scanning the laser radiation which are also used for the processing laser radiation, because only then is the aforementioned checking of the beam deflection possible. Thus, the region in which the reference structure is located is the potential processing zone.

If, on the other hand, an independent laser and beam deflecting unit is used for positional detection of the adapter by means of detection of the reference structure, an optically simpler structure may be achieved in some cases.

For the reference structure, any design of the adapter is suitable allowing detection of the position of the adapter. Conveniently, spatial zones will be designed which differ from the remaining beam path of the adapter in at least one optical property. Said optical property may be, for example, the reflection property or, more generally, the index of refraction of said spatial zone. The reference structure may then comprise, for example, control points or control lines, wherein back reflection, scatter or absorption or dispersion, respectively, of the radiation may characterize a spatial zone.

To distinguish the reference structure, a spectral range is a particularly suitable optical property which is above the UV absorption bands of optical materials, i.e. above 400 nm. A possible upper limit results from the desired spatial resolution and may typically be 2 µm. For the optical property, a spectral range of between 0.8 µm and 1.1 µm is preferably used. Depending on the spatial resolution, the marking structures may have dimensions of between 1 µm and 100 µm, preferably between 3 µm and 10 µm.

In principle, a great variety of mechanisms in the adapter are suitable to transmit to the output side the radiation supplied to the input side. For ophthalmic procedures, the adapter will be conveniently designed in the manner of a contact glass, so that the beam path comprises, at least in part, a material, in particular glass, which is transparent for processing laser radiation. In a particularly convenient embodiment, the adapter comprises a cylindrical or frusto-conical body one end surface of which is provided as the input side.

In addition, the adapter may have an output side which imparts a desired shape to a deformable surface of the object, e. g. by attaching the adapter to said deformable surface.

As already mentioned, the reference structure may allow to detect the actual spatial position of the adapter. Since the adapter is at the same time securely attached to the object, the actual position of the adapter also provides information on the position of the object relative to the laser processing device. Therefore, it is preferred for the reference structure to reflect the actual spatial position of the adapter. Thus, optical detection of the reference structure allows to obtain information on the orientation of the object relative to the laser processing device, so that the optical conditions for coupling-in of the laser beam on the object are known and high-precision laser processing is possible.

The laser processing device for the adapter according to the invention is capable of optically detecting the reference structure by means of the detecting unit and to consider in the control unit the thereby known actual position of the adapter for control of the beam deflecting unit. If the laser processing device is provided for the LASIK method, the control unit can consider the identified actual position for control such that the breakthroughs to be generated are located at the desired locations.

In this case, the treatment laser will usually operate in a pulsed manner. Therefore, in this respect an embodiment using a pulsed treatment laser is preferred for an ophthalmic procedure, wherein the object is the cornea and the control unit controls the beam deflecting unit and the treatment laser such that the laser beam generates optical breakthroughs at predetermined locations in the eye and, in doing so, respectively considers the identified actual position of the adapter or the desired shape of the cornea identified by said information.

As already mentioned, the reference structure of the adapter may serve to validate the function of the beam deflecting unit, e.g. of a scanning unit or of a zoom unit, during operation. It is therefore convenient that the laser processing device intermittently direct a laser beam, which may preferably also be the treatment laser beam, onto the reference structure by means of the beam deflecting unit deflecting the treatment laser beam, in order to check the operation of the beam deflecting unit. Any difference between the control of the beam deflecting unit and the known actual position of the reference structure may then be recognized in the further operation of the laser processing device. If such difference exceeds a certain limit value, the processing operation may be blocked.

Thus, a method is provided wherein the detection of borders between regions having different indices of refraction is effected, the position of said regions in the adapter being known and said regions being located in this component which is at least temporarily fixed to the laser processing device. Of course, the adapter may also be permanently attached, and not just temporarily. With a permanently attached adapter, the detection of the reference structure for checking the actual position of the adapter can also be carried out for maintenance purposes only during inspection work. The method comprises the steps of:

1. Mounting the adapter to the laser processing device.
2. Searching at least one reflector zone 25, wherein searching is understood to be automatic position determination within a spatial search area that is given by the expected location of the reflector zone 25. Position determination is effected in that (confocal) detection of the reflector zone 25 is carried out on the basis of the reflected or scattered signal of a laser beam, preferably of the treatment beam 4, whose focus 13 is three-dimensionally moved through the search area in a suitable manner by spatial shifting by means of the scanning unit 6 and the projection optics 9.
3. Storing the position thus determined, preferably for all three spatial directions. Steps 2 and 3 may be performed for some or all of the reflector zones.
4. Calculating the deviation as the difference between the measured location of the reflector zone and the expected position.
5. Checking the deviation for permitted values and considering the deviation in the beam deflection control, if possible.

It is a further object of the invention to improve an adapter or a laser processing device, respectively, of the aforementioned type such that it is not stringently required to work with a plane geometry.

In a further embodiment of the invention, this object is achieved by an adapter for coupling a laser processing device with an object to be processed, said object having a deformable surface, wherein the adapter comprises an input side which can be fixated relative to the laser processing device via a locking mechanism, has an output side which can be made to contact the deformable surface and to thereby impart a desired shape to it, with the adapter being attachable to the object, transmitting a laser beam along a beam path to the surface contacting the output side, said laser beam having been supplied, scanned over a certain region, to the input side by the laser processing device, wherein the adapter comprises marking structures in the beam path, which are optically detectable by means of the laser radiation scanned over said region and which encode information characterizing the adapter.

The object is further achieved by a laser processing device for such an adapter, said device comprising a beam deflecting unit for scanning a laser beam, a detecting unit for optical detection of the marking structures by means of the laser beam and a control unit reading out the detecting unit, said control unit controlling the beam deflecting unit, determining the information which characterizes the adapter and considering said information when controlling the beam deflecting unit. Thus, the reference structure previously used for adjustment of or for determining the position of the adapter, respectively, is now provided as marking structure serving to encode information. Of course, a combination is also possible.

The adapter usually serves to establish secure input-side coupling with the laser processing device. The adapter's input side which faces the laser processing device is therefore provided with suitable means for a secure connection to the output (e.g. distal end) of the laser processing device or its optical system, respectively, which output is directed toward the object, so that secure fixation with respect to the laser processing device is possible by means of a locking mechanism. For the locking mechanism it is conceivable, for example, to provide a flange surface on the adapter.

On its output side, the adapter ensures that the deformable surface of the object has a desired shape. Suitable means are provided for mounting the adapter to the object; in an ophthalmic application, a suction mounting means, e.g. a suction ring as known from WO 03/002008 A1 or from EP 1,159,986 A2, may be employed.

The marking structures provided in the beam path of the adapter allow the laser processing device to obtain information on the adapter used. Said information may be, for example, a model no. of the adapter, an individual designation or information on the desired shape which the adapter imparts to the deformable surface.

In order to provide said information directly to the laser processing device, the marking structures are arranged in the beam path such that they are optically detectable by means of the scanned laser radiation. Separate information transmission mechanisms may be obviated thereby; instead, the laser processing device may detect the marking structures by means of suitable laser beam sensing and, thus, extract the information characterizing the adapter.

The adapter as well as the laser processing device according to the invention enable the use of application-adjusted adapters without running the risk of erroneously working with operational parameters that do not suit the currently used adapter. This eliminates a possible source of error and increases the overall laser processing quality.

Conveniently, one will strive to use as few laser radiation sources as possible in the laser processing device, because any additional laser radiation sources will usually be connected with further costs. Thus, it is conceivable to use the laser beam emitted by the treatment laser also for optically detecting the reference structure. To do so, however, the peak intensity and the average power have to be reduced, on the one hand, in order to avoid stress on the object to be processed, i.e. the patient's eye, and to prevent, above all, a processing effect on the adapter. Therefore, it is convenient to provide a means for reducing the energy of the laser beam, said means at least temporarily reducing the energy of the laser beam emitted by the treatment laser for optical detection of the reference structure. For this purpose, e.g. an energy reducer may be coupled into or activated in the beam path. Alternatively, use can also be made of the property of conventional pulsed lasers, which consists in emitting background radiation of strongly reduced power between the individual laser pulses. Said background radiation can be used for detection of the reference structure, and an energy reducer can then be omitted.

At which position in the beam path the reference structure is located is not decisive for the adapter according to the invention; what is essential is merely that it should be possible to sense the reference structure by means of scanned laser radiation emitted by the laser processing device; thus, it is located within a space region in which the laser processing device can position the focus of the laser beam.

The laser radiation used in doing so may be identical with the processing laser radiation; however, this need not be the case. Conveniently, however, for scanning of the laser radiation the laser processing device will employ the same scanning unit which is also used for the treatment laser radiation. Thus, the region in which the reference structure is then located is the potential processing zone.

As marking structure, any design of the adapter is suitable which allows information to be retrievably stored within the beam path. The already mentioned design of spatial zones is particularly suitable. The marking structures may then be designed, for example, in a similar manner as a bar code, wherein back reflection, scatter or absorption or dispersion, respectively, of the radiation may characterize a spatial zone.

To distinguish the reference structure, a spectral range is a particularly suitable optical property which is above the UV absorption bands of optical materials, i.e. above 400 nm. A possible upper limit results from the desired spatial resolution and may typically be set at 2 µm. For the optical property, a spectral range of between 0.8 µm and 1.1 µm is preferably used. Depending on the spatial resolution, the reference structure may have dimensions of between 1 µm and 100 µm, preferably between 3 µm and 10 µm.

The information encoded by the marking structures may characterize whatever features of the adapter, e.g. geometric or material properties. A particularly preferred application is to be seen in describing the desired shape that is defined by the output side of the adapter, or in storing information about it. For example, the marking structures can represent the refractive properties of the desired shape.

As already mentioned, a convenient application for the adapter is the design as a contact glass for ophthalmic surgery. Of course, it may also be a special accessory which replaces the actual contact glass or is attached to the actual contact glass for the purpose of a measurement prior to treatment.

In one variant, the laser processing device according to the invention for the adapter according to the invention is capable of optically detecting the reference structure by means of the detecting unit and of considering it in the control unit in order to control the beam deflecting unit. If the laser processing device is designed for the LASIK procedure, the control unit can consider the desired shape identified by the information for control to obtain the breakthroughs to be generated at the desired locations.

BRIEF DESCRIPTION OF THE DRAWINGS

The invention will be explained in more detail below, by way of example and with reference to the Figures, wherein.

DETAILED DESCRIPTION OF THE INVENTION

Figure 1:
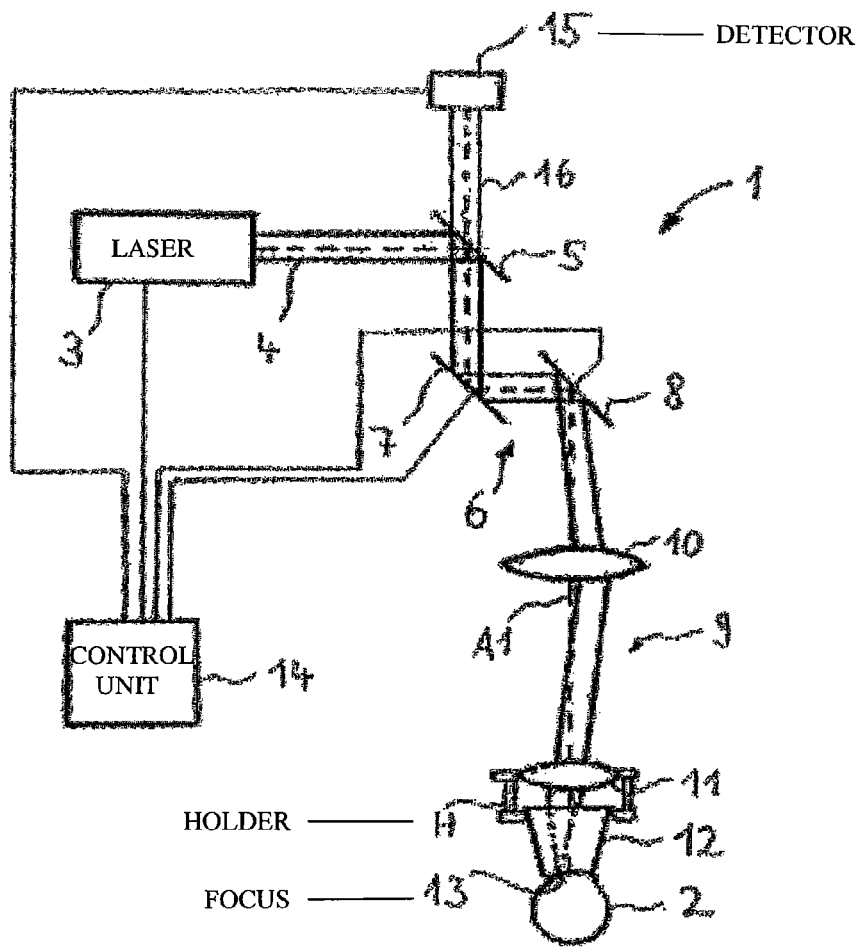
FIG. 1 shows a schematic view of a laser processing device for an ophthalmic procedure.

FIG. 1 shows a treatment device for an ophthalmic procedure, said device being similar to those described in EP 1,159,986 A1 and U.S. Pat. No. 5,549,632, respectively. The treatment device 1 of FIG. 1 serves to perform a correction of a visual defect in the eye 2 of a patient according to the known LASIK procedure. For this purpose, the treatment device 1 comprises a laser 3 which emits pulsed laser radiation. The pulse duration is e.g. in the femtosecond range, and the laser radiation is effective by means of non-linear effects in the cornea in the above-described manner. The treatment beam 4 emitted by the laser 3 along an optical axis A1 is incident on a beam splitter 5 which directs the treatment beam 4 onto a scanning unit 6. The scanning unit 6 comprises two scanning mirrors 7 and 8 which are rotatable about mutually orthogonal axes such that the scanning unit 6 two-dimensionally deflects the treatment beam 4. Adjustable projection optics 9 focus the treatment beam 4 onto or into the eye 2. For this purpose, the projection optics 9 comprise two lenses 10 and 11.

Arranged following the lens 11 is a contact glass 2 which is securely connected to the lens 11 and, thus, to the beam path of the treatment device 1 by a holder H. The contact glass 12, which is to be described in more detail, contacts the cornea of the eye 2. The optical combination of treatment device 1 and contact glass 2 attached thereto has the effect that the treatment beam 4 is concentrated in a focus 13 located in the cornea of the eye 2.

The scanning unit 6 is controlled via control lines (not identified in detail) of a control device 14, as are the laser 3 and the projection optics 9. In doing so, the control device 14 determines the position of the focus 13 both transversely to the optical axis A1 (through the scanning mirrors 7 and 8) as well as in the direction of the optical axis A1 (through the projection optics 9).

The control device 14 further reads out a detector 15 which reads out radiation scattered back from the cornea, said radiation passing through the beam splitter 5 as back reflection radiation 16. Confocal imaging may be used for this purpose. The role of the detector 15 will be discussed later.

The contact glass 12 ensures that the cornea of the eye 2 is given a desired shape. Due to the cornea 17 contacting the contact glass 12, the eye 2 is in a predetermined position relative to the contact glass 12 and, thus, to the treatment device 1 connected therewith.

Figure 2:
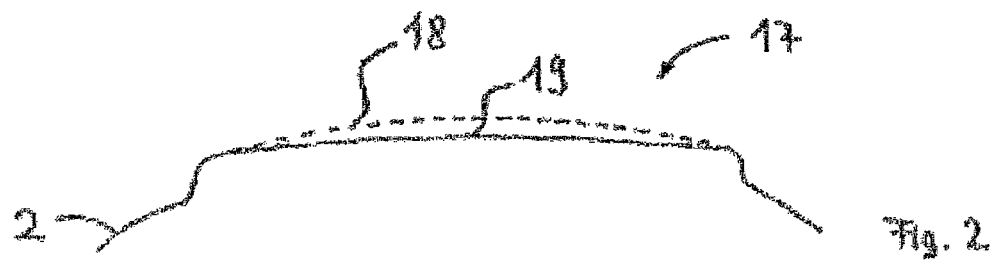
FIG. 2 shows a schematic view of the cornea of a patient.

This is schematically represented in FIG. 2, which shows a section through the cornea 17. In order to achieve exact positioning of the focus 13 in the cornea 17, the curvature of the cornea 17 has to be considered. The cornea 17 has an actual shape 18 which differs from patient to patient. The contact glass 12 now contacts the cornea 17 such that it deforms the cornea to a desired shape 19. The exact profile of the desired shape 19 depends on the curvature of the contact glass surface facing the eye 2. This will become clearer later with reference to FIG. 4. What is essential here is only that known geometrical and optical conditions are given by the contact glass 12 for directing and focussing the treatment beam 4 into the cornea 17. Since the cornea 17 contacts the contact glass 12, which is in turn stationary relative to the beam path of the treatment device 1 due to the holder H, precise three-dimensional positioning of the focus 13 in the cornea 17 is possible by controlling the scanning unit 6 as well as the adjustable projection optics 9.

Figure 3:
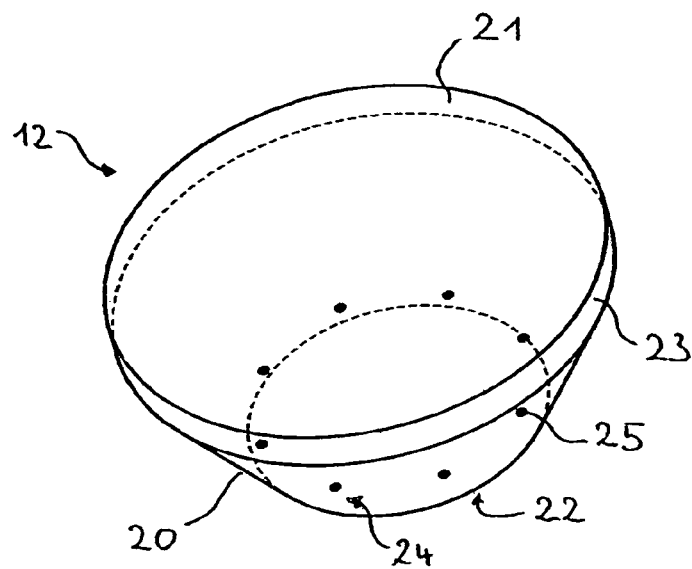
FIG. 3 shows a perspective view of a contact glass for the laser processing device of FIG. 1.

FIG. 3 shows a perspective view of the contact glass 12. As can be seen, the contact glass 12 comprises a glass body 20 which is transparent for the treatment beam 4. The treatment beam 4 is coupled in at an upper side 21 of the frustoconical glass body 20, which upper side 21 is assigned to the lens 11.

The cornea 17 contacts a lower side 22 of the contact glass 12. As the sectional view of FIG. 4 shows, the lower side 22 is curved in the desired shape 19 such that, when fully contacting the eye 2, it produces the desired shape of the cornea 17.

A flange surface 23 is provided on the contact glass 12 near the upper side 21, on which flange surface the contact glass 12 is fixated in the holder H by clamps. The flange surface 23 represents a mounting means being adapted to the holder H which includes a locking mechanism.

By mounting the body via the flange surface 23, the main axis of symmetry A2 of the frustoconical glass body 20 is adjusted in secure connection to the treatment device 21 and matching the optical axis A1. Inside the glass body 20 a reference structure 24 is formed, which is ring-shaped in the exemplary embodiment. In the exemplary embodiment, the distance from the main optical axis A2 is selected to be as great as possible, so that the reference structure 24 is located in the volume of the glass body 20 irradiated by the treatment beam 4 only if the treatment beam 4 is deflected at near-maximum.

Figure 4:
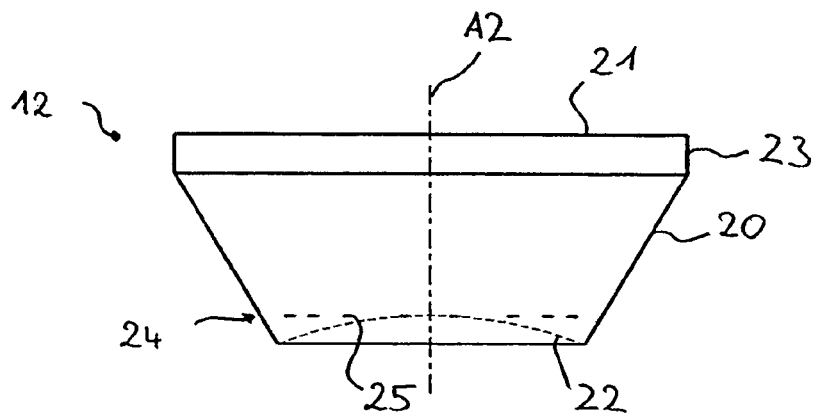
FIG. 4 shows a sectional view of the contact glass of FIG. 3.

As FIGS. 4 and 3 show, the reference structure 24 in the volume of the glass body 20 is preferably located on or near the periphery of the frustoconical glass body 20. The reference structure 24 consists of a plurality of reflector zones 25, which reflect the radiation emitted by the laser 3.

The reflector zone 25 may also be applied to the upper side 21 or the lower side 22 of the contact glass 12, i. e. to the input or output surface of the adapter, in the form of a suitable laminar structure or of suitable reflecting or non-reflecting layers. It is also possible to provide zones or layers with increased elastic scattering of light in order to realize the reflector zones 25.

If the treatment beam 4 is incident on a reflector zone 25, radiation energy is scattered back and is then picked up by the detector 15. Based on the signal from the detector 15, the control device 14 can thus recognize whether the treatment beam 4 is directed onto a reflector zone 25.

Figure 5:
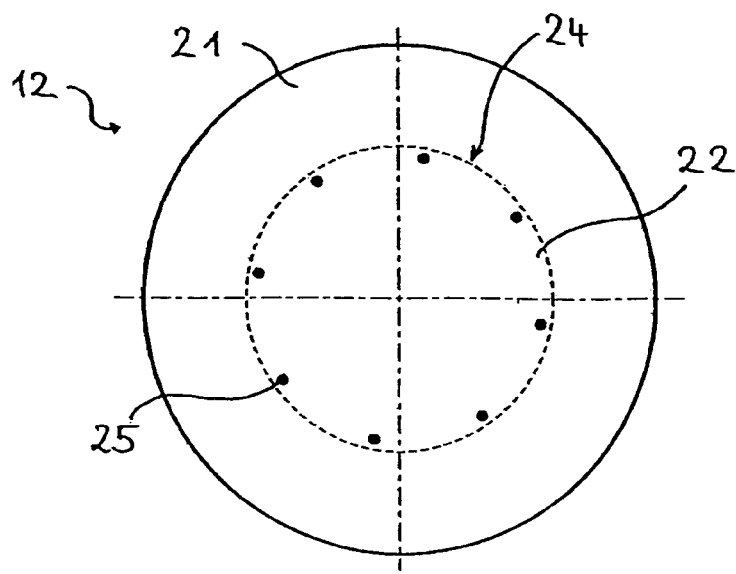
FIG. 5 shows a top view of the contact glass of FIG. 3.

As can be seen in FIG. 5, the reflector zones 25 are located near the periphery of the lower side 22 along a ring shape. Together with the deflection made possible by the scanning unit 6, the lower side 22 defines the size and location of the processing zone. In case of faulty positioning of the processing zone on the cornea 17, there will be a deviation between a desired and an achieved refraction result, so that a desired correction of a visual defect may sometimes not be achieved. The reflector zones 25 serve to compare the actual beam deflection with a predetermined desired value and to thereby minimize processing errors.

Deviations between the actual position of the beam and the predetermined desired position on the cornea 17 may be caused, in principle, by movements of the eye relative to the treatment device 1 or by faulty positioning of the eye 2 relative to the treatment device 1 or by faulty positioning of the scanning mirrors 7, 8 as well as of the projection optics 9. The contact glass 12 causes fixed positioning of the eye 2 relative to the treatment device 1, because the cornea 17 is fixed via suitable means, e.g. a suction ring (not shown in detail), at the eye 2. The reflector zones 25 now serve to be able to determine the position of the eye 2 relative to the treatment device 1.

The control device 14 controls the scanning unit 6 as well as the projection optics 9 such that a laser beam is passed over the reflector zones 25. For example, the control device 14 controls the laser 3 in a mode of operation in which a beam 4 having only a strongly reduced radiation intensity is emitted. This may be effected, for example, by activating or coupling in a suitable radiation attenuator. If the laser 3 is a pulsed source of laser radiation, a much weaker background radiation is possibly present also outside pulsed operation and can be used. Alternatively, it is possible to couple in an additional laser, for example via a further beam splitter being arranged preceding the scanning unit 3. Thus, said laser beam may either be the treatment beam 4, possibly attenuated in a suitable manner, or a separate laser beam which is coupled into the beam path along the optical axis A1 before it reaches the scanning unit 6.

If the laser beam impinges on a reflector zone 25, the detector 15 gives a corresponding signal. If a reflector zone 25 is thus detected, the control device 14 stores the thus given settings of the scanning unit 6 as well as of the projection optics 9. After scanning at least three reflector zones 25, a complete determination of the actual position of the contact glass 12 and, thus, of the cornea 17 is achieved thereby. The control device 14 uses said actual position in order to place the focus 13 at desired predetermined locations in the cornea 17 by means of the treatment beam 4 in subsequent treatment.

Due to the reference structure 24 along a ring at the periphery of the processing zone, unimpaired treatment is possible at the center of the cross-sectional surface which is circumscribed by the lower side 22 and through which the treatment laser beam 4 is coupled into the cornea 17. Given a sufficiently large numerical aperture of the treatment radiation, the influence of the reflector zones 25, which are located in the peripheral region of the processing zone, can be neglected during treatment.

The location of the reflector zones 25 at the periphery of the lower side 22 allows the function of the scanning unit 6 as well as of the projection optics 9 to be checked during current operation. In doing so, a relative deviation between the stored actual position of the reflector zones 25 as well as when again checking assigned settings of the scanning unit 6 and of the projection optics 9 may then be taken into account, in order to have deviations which occur during operation corrected or, as the case may be, to block operation of the treatment device 1 if there is too great a deviation.

Figure 6:
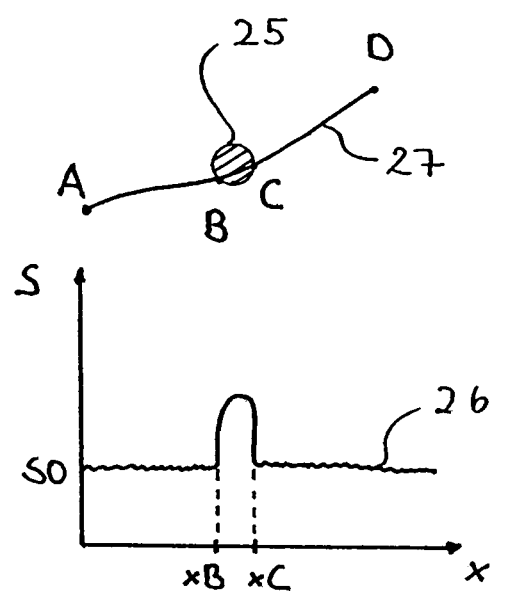
FIG. 6 shows a schematic view of the optical detection of a reference structure of the contact glass.

FIG. 6 illustrates the process of detecting a reflector zone 25. A signal S of the optical detector 15 is plotted therein as a curve 26. The focus 13 is guided from a point A to a point D along a path 27, which is usually three-dimensional, but is only represented two-dimensionally in FIG. 2, said point D covering the region in which a reflector zone 25 is expected. During movement of the laser focus 13 from point A, the detector 15 provides an idle value S0. Upon reaching point B, the signal changes and continuously increases, because back reflection occurs at the reflector zone 25. The respective coordinate xB in x-direction (the signal S is shown only one-dimensionally in FIG. 6 with respect to the x-direction) characterizes the beginning of the reflector zone 25 in the x-direction.

Upon reaching the point C, the signal drops back to the idle value S0, and the coordinate xC indicates the end of the reflector zone in the x-direction. If the diameter of the focus 13 is small as compared to the extent of the reflector zone 25 and, thus, small as compared to the distance BC, the clear separation of the leading edge at xB and the trailing edge at xC represented in FIG. 6 is possible. In this case, the obtained information on the location of these coordinates can be considered in the control device 14 when determining the position of the reflector zone 25, if the reflector zone 25 has a known shape. On the other hand, if the diameter of the laser focus 13 is equal to or greater than the distance BC, the coordinates xB and xC are undistinguishable and the center of the reflector zone 25 appears in the signal S.

The position determination by optical scanning, which is one-dimensionally described in FIG. 2, is of course effected in three space coordinates, so that the position of the reflector zone 25 is three-dimensionally determined finally.

Detection of the reflector zone 25 in the treatment device of FIG. 1 may preferably be confocally effected in order to obtain a maximum resolution along the optical axis A1 or A2, respectively (i. e. in the depth direction).

Figure 7:
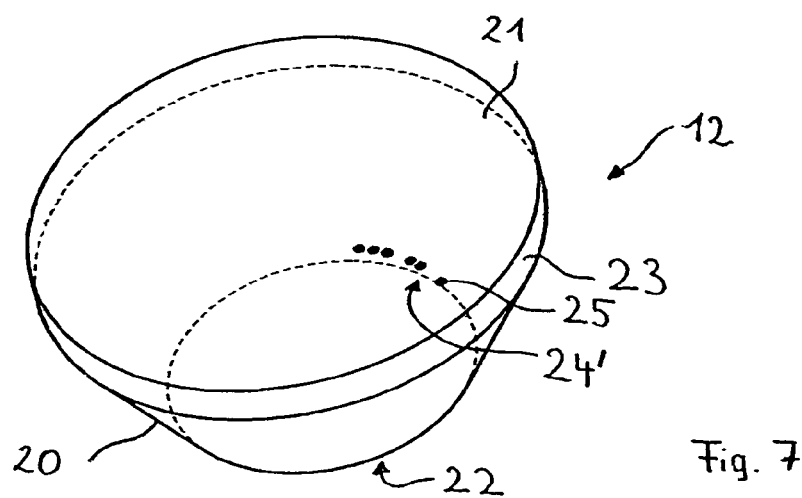
FIG. 7 shows a perspective view of a contact glass for the laser processing device of FIG. 1.
Figure 8:
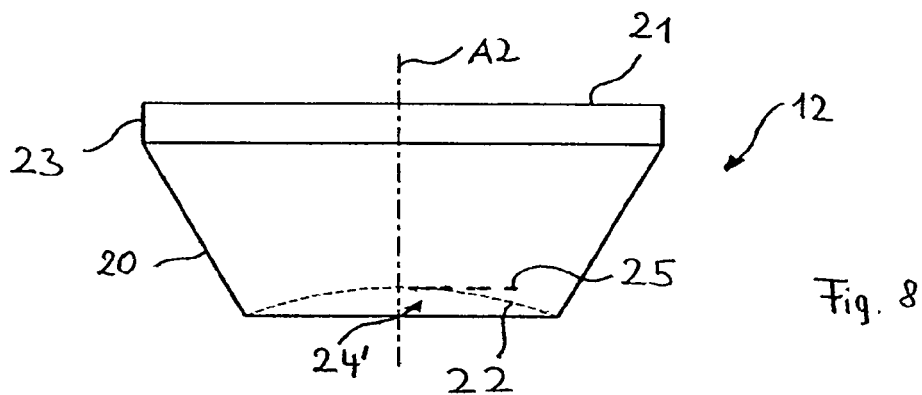
FIG. 8 shows a sectional view of the contact glass of FIG. 7.
Figure 9:
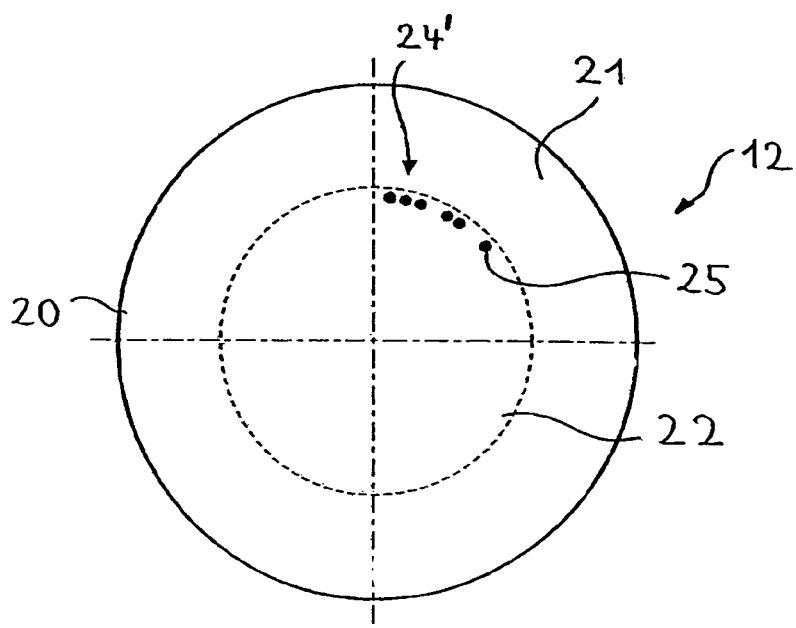
FIG. 9 shows a top view of the contact glass of FIG. 7.

FIGS. 7 to 9 show an adapter, which is designed as a contact glass 12, like that of FIGS. 3 to 5, but differs in the design of the reference structure. Due to the otherwise identical features, reference is made to the description of FIGS. 3 to 5, and the same reference numerals are used for the same features.

Inside the glass body 20 a code structure 24' is now formed as the reference structure, which follows a ring shape in the exemplary embodiment. In the exemplary embodiment, the distance from the main optical axis A2 is selected to be as great as possible, so that the code structure 24' is only located in the volume of the glass body 20 irradiated by the treatment beam 4 if the treatment beam 4 is deflected at near-maximum.

As FIGS. 4 and 3 show, the code structure 24' in the volume of the glass body 20 is preferably located on or near the periphery of the frustoconical glass body 20. The code structure 24' consists of a plurality of reflector zones 25, which reflect the radiation emitted by the laser 3. If the treatment beam 4 is incident on a reflector zone 25, radiation energy is back-scattered, which is then picked up by the detector 15.

The reflector zone 25 may also be applied to the upper side 21 or the lower side 22 of the contact glass 12, i. e. to the input or output surface of the adapter, in the form of a suitable laminar structure or of suitable reflecting or non-reflecting layers. It is also possible to provide zones or layers with increased elastic scattering of light in order to realize the reflector zones 25.

Based on the signal from the detector 15, the control unit 14 can thus recognize that the treatment beam 4 is directed onto a reflector zone 25. In total, the series of annularly arranged reflector zones 25 in the code structure 24' thus provides an encoded signal, which in the exemplary embodiment represents the curvature of the lower side 22 of the glass body 20 and, thus, the geometry of the desired shape 19 which the cornea 17 has with the contact glass 12 applied thereon. Thus, the code structure 24' realizes marking structures which identify or describe the contact glass 12.

In order to carry out this information extraction, which was already mentioned in principle, the control device 14, on the one hand, controls the laser 3 into an operating mode in which only a beam 4 with a strongly reduced radiation intensity is emitted. This may be effected, for example, by activating or coupling in a suitable radiation attenuator. If the laser 3 is a pulsed source of laser radiation, a much weaker background radiation is possibly present also outside pulsed operation and can be used.

Alternatively, it is possible to couple in an additional laser, for example via a further beam splitter being arranged preceding the scanning unit 3. Thus, said laser beam may either be the treatment beam 4, possibly attenuated in a suitable manner, or a separate laser beam which is coupled into the beam path along the optical axis A1 so as to precede the scanning unit 6.

In order to read out the code structure 24', the control device 14 controls the projection optics 9 as well as the scanning unit 6 such that the focus of the laser radiation passes over the region in which the code structure 24' is expected. The back reflections are recognized in the signal of the detector 15, are assigned to the actual focus position and are evaluated with regard to the encoded information with the help of suitable means (for example, suitable processing electronics and a memory element). Detection of the reflector zone 25 in the treatment device of FIG. 1 may preferably be confocally effected in order to obtain a maximum resolution along the optical axis A1 or A2, respectively (i. e. in the depth direction).

The information thus obtained about the adapter is then considered by the control device 14 during the subsequent treatment of the cornea 17. For example, focus 13 is controlled by the scanning unit 6 and the projection optics 9 such that the desired shape 19 of the currently used contact glass 12 is considered. Alternatively, the treatment device 1 may also be blocked after having scanned an unsuitable contact glass, in order to make treatment impossible. Additionally or alternatively, corresponding information on the currently used contact glass may be output by suitable means.

The invention claimed is:

1. An adapter for coupling an eye to be treated in ophthalmic surgery with a laser treatment device comprising a scanning device for scanning a laser beam, the adapter comprising:
   an adapter input side, being fixable relative to the laser treatment device via a locking mechanism;
   an adapter beam path,
   a scanned region being part of the adapter input side, wherein the laser beam having been supplied to the scanned region is transmitted along the adapter beam path to the eye, wherein the adapter beam path starts at the scanned region and the laser beam passes through the scanned region and along the adapter beam path when being scanned during laser treatment; and
   a reference structure, the reference structure being located in the adapter beam path such that the reference structure can be illuminated by laser radiation being scanned over the scanned region, wherein the reference structure is adapted to absorb or reflect the laser radiation to make the reference structure optically detectable;
   wherein the reference structure is located in a known position relative to the adapter and scanning of the reference structure by the scanned laser beam allows the laser treatment device to detect the position of the adapter.

2. The adapter as claimed in claim 1, further comprising an adapter output side, through which laser radiation supplied to the region of the adapter input side exits and which can be brought into contact with the cornea of the eye and thereby imparts a desired shape to the cornea.

3. The adapter as claimed in claim 1, wherein the marking structure comprises spatial zones which are located within the adapter beam path and which differ from a remainder of the adapter beam path in at least one optical property.

4. The adapter as claimed in claim 3, wherein the optical property comprises refractive index.

5. The adapter as claimed in claim 1, wherein the adapter beam path apart from the reference structure comprises a material which is transparent to the laser radiation.

6. The adapter as claimed in claim 2, further comprising a substantially cylindrical or substantially frustoconical body, one end surface of which acts as the adapter output side, the adapter output side conforming to the desired shape of the cornea.

7. The adapter as claimed in claim 2, further comprising a substantially cylindrical or substantially frustoconical body, one end surface of which acts as the adapter input side.

8. The adapter as claimed in claim 1, further comprising a flange for engagement to the locking mechanism.

9. The adapter as claimed in claim 1, further comprising a suction portion for attachment to the eye.

10. The adapter as claimed in claim 1, wherein the information encoded includes the desired shape defined by the adapter output side.

11. The adapter as claimed in claim 1, wherein the information encoded includes refractive properties of the adapter output side.

12. The adapter as claimed in claim 1, wherein the adapter comprises a contact glass for eye surgery.

13. Laser treatment device emitting a laser beam and comprising:
   a laser emitting a laser beam adapted for treating an object;
   a beam scanning unit for scanning the laser beam over the object to be treated:
   an adapter, having an adapter input side, the adapter being fixable relative to the laser treatment device via a locking mechanism,
   the adapter being capable of being brought into contact with the object to position the object relative to the laser treatment device, wherein the adapter comprises an adapter beam path and a scanned region being part of the adapter input side, wherein the laser beam having been scanned over the adapter scanned region is transmitted along the adapter beam path to the object, and a reference structure located in the adapter beam path wherein the adapter beam path starts at the scanned region and the laser beam passes through the scanned region and along the adapter beam path when being scanned during laser treatment;

a control unit controlling the laser to operate in an illuminating mode; and a detecting unit for optical detection of the reference structure illuminated by the laser beam emitted in the illuminating mode, wherein the control unit receives output from the detecting unit and controls in the illuminating mode the beam deflecting unit to scan the laser beam over the scanned region such that the reference structure is illuminated by the laser beam and determines an actual position of the adapter on the basis of the actual scanning position of the scanned laser beam and the output of the detecting unit during the illuminating mode;

wherein the reference structure is located in a known position relative to the adapter and scanning of the reference structure by the scanned laser beam allows the laser treatment device to detect the position of the adapter.

14. The laser treatment device as claimed in claim 13, wherein the control unit controls the laser in the illuminating mode such that the laser beam has no machining effect to the adapter.

15. The laser treatment device as claimed in claim 14, wherein the control unit determines a difference between the desired position and the actual position of the adapter and blocks treatment if the difference exceeds a threshold value.

16. A laser treatment device for application of energy of a laser beam to a deformable surface of an object, the laser treatment device comprising:

a laser emitting the laser beam;

a beam deflecting unit that scans the laser beam over the object to be treated:

an adapter having an adapter input side, which can be fixated via a locking mechanism;

the adapter comprising an adapter beam path and a scanned region being part of the adapter input side wherein the adapter beam path starts at the scanned region and the laser beam passes through the scanned region and along the adapter beam path when being scanned during laser treatment, wherein said laser beam having been scanned over the scanned region, is transmitted along the adapter beam path to the object and the adapter including a reference structure, the reference structure being located in the adapter beam path and being located in a known position relative to the adapter and wherein scanning of the reference structure by the scanned laser beam allows the laser treatment device to detect the position of the adapter;

the adapter including an adapter output side which can be brought into contact with the deformable surface to position the object relative to the laser treatment device and which imparts a desired shape to the deformable surface when the adapter is in contact with the object, and wherein the reference structure comprises marking structures which encode information about the adapter;

a control unit controlling the laser to operate in an illuminating mode; and a detecting unit for optical detection of the reference structures illuminated by the laser beam emitted in the illuminating mode, and wherein the control unit receives output from the detecting unit, controls in the illuminating mode the beam deflecting unit to scan the laser beam over the scanning region to illuminate the reference structure and determines the information about the adapter.

17. The laser treatment device as claimed in claim 16, further comprising a pulsed treatment laser for an ophthalmic procedure, wherein the object comprises the cornea, and the control unit controls the beam deflecting unit and the treatment laser such that the laser beam generates optical breakthroughs at predetermined locations in the cornea and, in doing so, considers the desired shape of the surface of the cornea, and wherein the desired shape is identified by said information.

18. The laser treatment device as claimed in claim 16, wherein the laser is a pulsed treatment laser for an ophthalmic procedure and comprises a device for attenuating laser beam energy in the illuminating mode to avoid any machining effect to the adapter when optically detecting the reference structure.

19. The laser treatment device as claimed in claim 13, wherein the control unit considers the determined actual position when controlling the beam deflecting unit.

20. The laser treatment device as claimed in claim 16, wherein the control unit considers the information when controlling the beam deflecting unit.

21. The laser treatment device as claimed in claim 13, and wherein the reference structure comprises marking structures which encode information about the adapter.

22. The laser treatment device as claimed in claim 16, and wherein the reference structure comprises marking structures which encode information about the adapter.

23. The adapter as claimed in claim 1, wherein the adapter can be brought into contact with the eye to position the eye relative to the laser treatment device and wherein the reference structure comprises marking structures which encode information about the adapter.

* * * * *